United States Patent [19]

Schmidt et al.

[11] 4,407,008

[45] Sep. 27, 1983

[54] METHOD AND APPARATUS FOR LIGHT-INDUCED SCANNING-MICROSCOPE DISPLAY OF SPECIMEN PARAMETERS AND OF THEIR DISTRIBUTION

[75] Inventors: Werner Schmidt; Gerhard Mueller, both of Aalen; Klaus Weber, Konigsbronn; Volker Wilke, Aalen, all of Fed. Rep. of Germany

[73] Assignee: Carl Zeiss-Stiftung, Oberkochen, Fed. Rep. of Germany

[21] Appl. No.: 309,371

[22] Filed: Oct. 7, 1981

[30] Foreign Application Priority Data

Oct. 8, 1980 [DE] Fed. Rep. of Germany ....... 3037983

[51] Int. Cl.$^3$ .............................................. H09N 7/18
[52] U.S. Cl. ..................... 358/93; 356/301; 356/318
[58] Field of Search ................ 358/93; 356/301, 317, 356/318

[56] References Cited

U.S. PATENT DOCUMENTS

4,030,827 6/1977 Delhaye ............................. 356/318
4,195,930 4/1980 Delhaye ............................. 356/301

*Primary Examiner*—Howard Britton
*Attorney, Agent, or Firm*—Hopgood, Calimafde, Kalil, Blaustein & Judlowe

[57] ABSTRACT

The invention contemplates scanning-microscope display of plural observed parameters of an examined specimen, where the parameters derive from flying-spot light-exposure of the specimen, and where at least one of the observed parameters is outside the wavelength range of the flying-spot. In some illustrative embodiments, at least one of the observed parameters is sensed by a detector which uses the same scanning optics as the flying-spot, and in other embodiments other techniques of synchronization are involved. The disclosed embodiments also provide for selective arrest of scanning to enable such factors as fading fluorescence and spectrum analysis to be ascertained strictly for a surface occlusion, impurity or other anomaly of interest.

27 Claims, 6 Drawing Figures

METHOD AND APPARATUS FOR LIGHT-INDUCED SCANNING-MICROSCOPE DISPLAY OF SPECIMEN PARAMETERS AND OF THEIR DISTRIBUTION

BACKGROUND OF THE INVENTION

The present invention relates to a method for the light-induced scanning-microscope display of a plurality of specimen parameters and of their distribution, as well as to apparatus for carrying out this method.

Various methods of analysis, optimalized for specific applications (chromatography, mass-spectrometry) which do not permit non-destructive measurement, are used at the present time for reliable specimen analysis.

With the spectral-photometric methods of analysis known up to the present time, however, the specimen to be examined cannot always be unequivocally identified, since involved weakly structured absorption spectra do not have any particularly great informational content. In particular, difficulties result when the specimen contains several substances having overlapping spectra. With known methods of optical analysis, one generally obtains merely integral information concerning the samples to be examined; nothing can be said with regard to the relative distribution of their parameters.

In the "Mikroprobe Mole" prospectus of Jobin Yvon Company and in GIT journal *Laboratorium I*, 1978, page 38, a method is described for the microanalytic examination of specimens in which they are continuously irradiated with laser light and observed in the light of their emitted Raman radiation. It is possible to use only light of characteristic Raman lines of given substances contained in the examined specimen, the relative distribution of which substances is to be determined. Depending on the adjustment of the monochromator used for observation, it is possible to produce substance-specific images of the specimen which are also informative as to the molecular structure of the components.

The sensitivity of this method is, to be sure, limited, since a laser of fixed wavelength is used to illuminate the entire region of the specimen; thus, high suppression of scattered light is necessary. Fluorescing specimen regions further reduce the sensitivity of the apparatus.

Furthermore, since the entire image of the surface of the specimen is transmitted through the monochromator, the obtainable resolution is limited.

In the particular case of lengthy short-wave light irradiation of sensitive specimens, damage to the object cannot be prevented. In actual use, this method is limited to specimens which supply a sufficiently intensive characteristic Raman spectrum. However, this is true only for molecules in which molecular vibration results in a significant change in polarizability.

In *Journal of Raman Spectroscopy*, No. 3 (1975), pages 33 to 43, mention is made of an arrangement for Raman microscopy which relies on laser-beam unidimensional scanning of a specimen moved perpendicular to the scanning direction, and electronic creation of the image is based on photo-multiplier signals selected in phase with the scanning frequency. Through raster-like scanning of the specimen one obtains, in light of the characteristic Raman radiation, specimen images which are of high definition, thereby obtaining greater sensitivity than in methods in which the entire surface to be examined is illuminated. Radiation damage to the material, which might occur, for example, in the case of geological specimens is minimized with raster-like scanning. The aforementioned sensitivity problems caused by fluorescent light, however, also occur with this known arrangement, since in both cases an entire scanning line is focused on the photo-multiplier.

GENERAL DISCUSSION OF THE INVENTION

The object of the present invention is to provide a method of optical analysis which permits identification of specimen-specific parameters with high sensitivity and the measurement of their two-dimensional distribution with high resolution, and to provide for performing this method with apparatus of the simplest possible construction.

The first part of this goal is achieved by detecting at least two different radiation components, at least one of which lies in a spectral region outside that of the illumination, and at least one of the two components is focused on a stationary receiver via the objective used for focusing the scanning beam and the scanning unit used for beam deflection.

The method of the invention permits a non-destructive analysis, as distinguished from methods of mass-spectroscopy and micro-plasma probes; additionally, the method can be used for a large number of substances, using various spectroscopic detection techniques, depending upon the specific application.

Thus, radiation emitted by the specimen may contain, for instance, fluorescence, phosphorescence or Raman radiation, usable for display of the image. The position and width of the desired spectral region can be suitably controlled in accordance with the specific application, by selection of suitable filters and detectors.

The method is by no means limited to illumination with light in the visible spectral region, but it can easily be seen that radiation of other wavelengths (IR, UV) can also be used if the specific problem so requires. The same is true for emitted radiation. The expression, "radiation not contained in the illumination spectrum", should be understood to mean not only electromagnetic radiation but rather, in a wider sense, any form of detectable specimen parameters. This may also be corpuscular radiation, consisting, for instance, of photoelectrons emitted by the specimen. Such a method, in which light-induced emission of photoelectrons is used to produce the image, may be employed wherever high resolving power in the scanning electron microscope is not required, thus making it possible to obtain images of high contrast in the "light" of electrons from the highest occupied levels of the molecular structure of the specimen. In thus creating the image, the object is not damaged by an energy-rich electron beam.

In an illustrative situation involving two detectors for separate detection of scattered light and Raman light at a characteristic wavelength, one may determine a distribution of the substance to be analyzed, in coordinated relation to the visible structure of the substance. The distribution of a substance identified by Raman radiation without simultaneous reference to the visible structure is generally completely valueless (determination of position of inclusions in cells). But with the indicated two detectors, even slight radiation that is characteristic for the examined specimen can be distinguished against background noise. Furthermore, coincident or anti-coincident display of different components of the substance can be realized with high sensitivity of detection.

Since the detected radiation and the illuminating light are accommodated by the same scanning device, only the currently illuminated point of the specimen is imaged on a stationary receiver; thus, the detector is not exposed to radiation which comes from regions of the specimen which have already been scanned (persisting fluorescence) and which could otherwise produce a disturbing increase in the signal background. The expense of the process is furthermore comparatively slight since certain parts (scanning unit, objective) have multiple uses. Thus, use of a high-aperture, well-corrected objective enables object-plane focusing of the illumination beam, wherein focus is limited only by refraction; as a result, resolution is optimized in the images produced. On the other hand, a maximum amount of light intensity is obtained upon detection of specimen radiation.

The latter feature is particularly advantageous when detecting radiation which is not contained in the illumination spectrum (fluorescence, Raman radiation) and which lies several orders of magnitude below the intensity of the excitation light. Particular advantages are obtained if two or more signal wave trains are produced substantially simultaneously, e.g., by detection of the transmitted radiation, the scattered radiation, the fluorescence or the Raman radiation, and if these separate signal wave trains are used to produce the image, as shown by the following examples.

(a) Scattered Radiation—Transmission

By measuring both components of the radiation and with suitable display one obtains an image which reproduces the distribution of absorption in the specimen, i.e. a transmitted-light bright-field image which is based solely on absorption and does not reproduce any scattering structures. The same information may also be obtained by a method in which a beam of light modulated at low frequency scans a specimen, and heat waves produced by light absorption in the specimen are detected by an infrared sensor (photothermal effect) and then used for production of the image. Additionally, this method enables measurement of the two-dimensional distribution of the absorption properties of a specimen. The method is particularly suitable for examination of opaque specimens, in that it enables controller depth-resolution by selective variation of the light-modulation frequency. At present, it is known that the photothermal effect can be used for detection of absorption spectra, but the production of images by means of the effect has not been known.

As was the case for detection of specimen-emitted photo-electrons, in the production of an image the photothermal detector in question must be arranged outside the illumination optics since the latter in general do not transmit such radiation. However, the illumination optics in such cases has additional use in the production of a bright-field image from visible light.

(b) Scattered Radiation—Fluorescence

A dark-field image and a concurrent display of fluorescing specimen regions are obtained, and it is possible, by suitable selection of the spectral region, to selectively recognize the relative position of the different fluorescent particles, for instance impurities, in the specimen.

(c) Transmission—Flourescence

As a modification of (b), the fluorescence image can be compared with a bright-field image.

(d) Scattered Radiation—Raman Radiation

In their position relative to visible structures in the dark-field image, it is possible to observe inclusions, surface defects and absorbed substances, the molecular structure of which can be unequivocally identified by their emitted Raman radiation.

(e) Transmission—Raman Radiation

It is possible to observe metabolism in living organisms without any damage to the object occurring as a result of a long period of radiation and high radiation intensity. The different metabolic products give different Raman spectra so that their specific distribution in the organism can be determined by observation in the characteristic Raman light. Due to the strict dependence of the intensity of the Raman lines on the concentration of the substances contributing thereto, a quantitative evaluation of several superposed spectra is also possible.

(f) Fluorescence—Raman Radiation

Simultaneous measurement of the Raman intensity and of the intensity of the fluorescent light permits a display of the specimen in Raman light (subtraction) which is not corrupted by the fluorescent background. Discrimination of the Raman radiation from the fluorescence can be effected by utilization of the fluorescence decay time or, with a knowledge of the spectra, by suitable selection of the spectral region in which the two radiation components are detected.

(g) Raman Radiation—Raman Radiation

In this case, simultaneous identification of several different components of a specimen is possible; and, in the even of suitable superposition of the images, display in relative concentration is also possible. Instead of two detectors adapted to different Raman lines, it is also possible, of course, to use two monochromatic sources of light of different wavelengths, and to alternately illuminate the specimen at these different wavelengths.

It may prove advantageous to additionally irradiate the specimen with ultrasonics, as when examining opaque solids for inclusions or inhomogeneities below the surface of the specimen. Stray radiation, modulated at an ultrasonic frequency at the surface, gives an image of the internal structure of the specimen and can be compared with the surface-specific images in Raman or fluorescent light. In this connection, relationships between inner and outer specimen structure become visible.

Furthermore, time-variation of the specimen surface can be observed in Raman or fluorescent light during the ultrasonic irradiation. Ultrasonic purification processes can be thus monitored. Through simultaneous observation of the scattered light (from which the distribution of the ultrasonic amplitudes on the surface of the specimen can be determined) and of the Raman light (from which the three-dimensional distribution of impurity concentration results), it is possible to achieve material-specific optimizing of the duration and amplitude of the ultrasonic frequency.

Display of detector-output signals as images of the specimen surface can be effected in various ways. If correlation exists between structures as displayed in different spectral regions, it is advantageous to show them superposed in a single image. For this purpose, one may create a display in which two display images alternate in time, details which are not present in both images being offered the observer by blinking.

To eliminate background in the presentation of a single image it is advantageous to take the difference between the output signals of two detectors, one of which is sensitive to a wavelength characteristic of the substance and the other to a somewhat different wavelength. If the non-correlated distribution of different substances identified by radiation in different spectral regions is displayed, then a single image display appears advantageous.

Electronic amplitude and/or phase control of output signals of the different detectors may be employed to enhance contrast and to produce the above-mentioned superposed images. For example, using signal differentiation, it is possible to obtain a better recognition of object contours, and display contrast can be enhanced by logic operations (division, subtraction) on the signals of two detectors. These measures can be carried out at little expense for the electronic system and thus make conventional optical-contrasting techniques (phase-contrast, etc.) unnecessary.

Another advantageous contrasting possibility is obtained for the case of images produced by means of light which is elastically scattered on the specimen if the illumination is coherent. By superposing light from the observation ray path on the scattered light, contrast-enhancing interference can be produced at the detector.

If a monomode laser is used to illuminate the specimen, then the resolving power can be improved (as compared with conventional microscopic imaging), particularly for the case of producing an image in Rayleigh-scattered light, which is a coherent scatter process; such improvement may be achieved in the following manner: Object points successively illuminated by the scanning process provide a distribution of signal intensity along a scan line, which distribution corresponds to the convoluting of the object function with the intensity function of the light spot at the focus of the objective used. The latter function can be well approximated, for instance, by a Gaussian function. It is now advisable and possible, with known methods of data processing, to unfold the measured intensity distribution of scattered light along a scan line in order to arrive at an over-resolution of the specimen which is no longer diffraction-limited by direct reproduction of the object function obtained thereby. The obtainable resolution is then dependent only on the obtainable precision of measurement of the individual intensities of the grid of points with which the specimen is scanned.

Deconvolution can be carried out with reasonable electronic expenditure in real time along a scan line; for deconvolution of two-dimensional intensity functions, the specimen must be scanned with very small shift, and the measured intensity distribution along each scan line must be stored, the deconvolution being effected by a subsequent mathematical process.

In the analysis of complicated compounds, it is advisable, in addition to the indicated method, to arrest raster-deflection of the light bundle at preselected local image regions and to continuously vary the given spectral region or regions in order to write a spectrum or combination of spectra from pre-selected image regions; based on such spectrum or spectra, local structures can be precisely identified according to their molecular composition. In this way, an objective optimization of the "wavelength" parameter is also possible, to obtain high-contrast images of the distributions of the substances identified.

Of course, in certain applications (for instance in the detection of Raman radiation), the wavelength of the illuminating light can also be varied, instead of varying the spectral sensitivity of the detector; this is an equivalent measure with which, aside from special cases (such as resonance-Raman-scattering), the same spectra are obtained as with a continuously variable monochromator in front of the detector.

Specifically, when observing Raman light of different wavelengths, it may be advisable instead of using two detectors which are adapted, for instance, by suitable filters to the desired wavelength region, to employ two monochromatic light sources and to irradiate the test specimen simultaneously or alternately with light of plural wavelengths. In the former case, the respective intensities of corresponding lines from two Raman spectra are superposed; but in the second case, it is possible, in alternation, (a) to effectively eliminate background radiation by taking the difference between two signals which succeed each other in time, or (b) to create a display of the relative concentration of two sample substances.

The method of the invention is used to advantage in quality control of hyperpure materials in biomedicine, in production of pharmaceuticals, and in industrial chemistry. Its field of use is wherever a sensitive method is required for the non-destructive examination or analysis of the molecular structure of specimens. In illustration of a first-field (biomedicine) situation, the surface character of implants may be verified, for implant resistance to corrosion, and for implant compatibility with the host organism.

Illustrative of second-field situation, mention may be made of routine control of hyperpure drugs whose therapeutic effect may depend strongly on only slight changes in their composition. The molecular structure or the concentration of the drugs examined can be clearly recognized by means of detectors which are tuned to the characteristic Raman lines of the components, and they can thus be continuously monitored.

The invention also concerns an apparatus for the light-induced scanning-microscope display of specimen parameters and of their distribution, in which apparatus certain optical components are interposed between source of illumination and the specimen, these components comprising first of all a splitting mirror and then means for raster-deflection of the beam of light, followed by an objective for focusing the bundle of light on the specimen; radiation emitted from the specimen is focused on at least one stationary detector by the objective, the deflection means and the splitting mirror, as well as subsequent filters to suppress the illumination spectrum.

This apparatus permits selective detection only of radiation emitted from the illuminated point of the specimen. Due to a constant imaging ratio between the illuminated scanning spot on the specimen and the detector or diaphragm on which the illuminated spot is continuously focused throughout the scan process, a continuously variable monochromator can be employed without difficulty, thus permitting selective adjustment of the spectral region in which the method is performed. In an alternative situation, the continuously variable monochromator can be replaced by a monochromator which spectrally disperses radiation and which directs the dispersed radiation to a plurality of receivers associated with the individual spectral regions.

If the nature of the different radiations is so different (e.g. visible light, electron-beam, long-wave infrared radiation, sound) that transmission by the illumination optics is not possible, a modified or second apparatus is used. In such apparatus, the optical components interposed between the light source and the specimen again comprise a splitting mirror and means for raster-deflection of the light beam, and then an objective for focusing the light bundle on the specimen; radiation emitted from the specimen is focused on at least one stationary detector by the objective, the deflection means and the splitting mirror, and at least one second receiver responsive to radiation outside the illumination spectrum is disposed in front of or behind the specimen and outside of the optical system containing the deflection unit.

Delayed emission from a given point in the field of scanning the specimen can be specifically measured by positioning a diaphragm in front of the detector, the positioning being (a) in such lateral offset from the optical axis of the spot-imaging system, and (b) in the direction of offset opposite to the direction of scanning-spot motion, that it is the delayed emission that is sensed by the detector, it being understood that the extent of such diaphragm offset is a function of scan speed, for a given delay time.

If a linear diode array is used in place of the diaphragm, and if it is oriented as above-described in the direction of scanning-spot motion and with suitable filtering to assure response to a given wavelength range, then one may obtain a display of the fading luminescence of all image points, the latter display having resolution quality which depends upon the number of elements in the array. By means of suitable trigger circuits, such fading behavior can be selectively displayed, either for the entire image region as a whole, or only for selected image points. It is thus possible, on the basis of different luminescence-fading times, to recognize different components of a specimen and to discriminate between them in the pictorial display. A differentiation between Raman radiation (which is emitted practically without delay), and fluorescence or phosphorescence, is thus possible with the indicated technique.

A laser may be advantageously employed as the light source, particularly if importance is placed on the detection of Raman radiation, for which a monochromatic source of light is required. The laser may, for example, emit light continuously and be continuously variable, for spectralphotometric purposes or in order to obtain Raman spectra. If higher power densities of illumination radiation are desired, as may be necessary for fluorescence excitation or in order to reduce to sharply delimited points the image regions to be scanned, it is preferred to employ a pulsed laser, the pulse train being synchronized with the deflection unit and with the electronic image-producing apparatus. An additional gain in sensitivity may then be obtained by gated suppression of the detector output signal, in periods between light pulses.

Of course, other sources of light can also be used for particular applications, for example, incandescent bulbs or gas-discharge lamps. If high radiation densities are to be obtained within a limited spectral region, a light-emitting diode will be used as the source of light. Light-emitting diodes are also preferred for infrared absorption and reflection measurements.

In apparatus for the light-induced scanning-microscope display of specimen parameters and of their distribution, the invention provides a splitting mirror behind a light source such as a laser or luminescence diode array, and behind the splitting mirror an objective focuses the light source at the plane of the object; radiation emitted from the specimen is focused by the objective and the splitting mirror onto a detector diode array, and an electronic system is provided for synchronous excitation or scanning of conjugate diodes of the two arrays, in each case by the same optical system.

The apparatus just described avoids mechanical scanning components and therefore is of particularly simple construction. Nevertheless, there is assurance that in each case the only detected radiation is from the region of the specimen point which is currently illuminated, since scanning takes place synchronously on both the illumination and the detection sides of the system. Both one-dimensional and two-dimensional arrays can be used for scanning and detection. In the former case, production of a two-dimensional image requires physical displacement of the specimen in the direction perpendicular to the scanning line.

If the specimen to be examined is placed in the specimen chamber of a scanning electron microscope, it is then possible, (a) in addition to examinations with a high-energy electron beam, which are necessary for analysis of atomic structure, (b) to determine molecular properties by analysis of displayed two-dimensional distribution of emitted-photoelectron measurements made in the context of irradiating light of particular different wavelengths. It is furthermore possible to make control checks in the course of preparing a specimen (ion etching, vaporization treatment) using optical techniques prior to making the electron-microscopic examination. For example, the specimen may be observed, during an ion-etching process, in the light of its Raman radiation, and in this way it can be determined when the etching process is at an end.

DETAILED DESCRIPTION OF THE INVENTION

Various embodiments of the invention will be described in conjunction with the accompanying drawings, in which.

Figure 1:
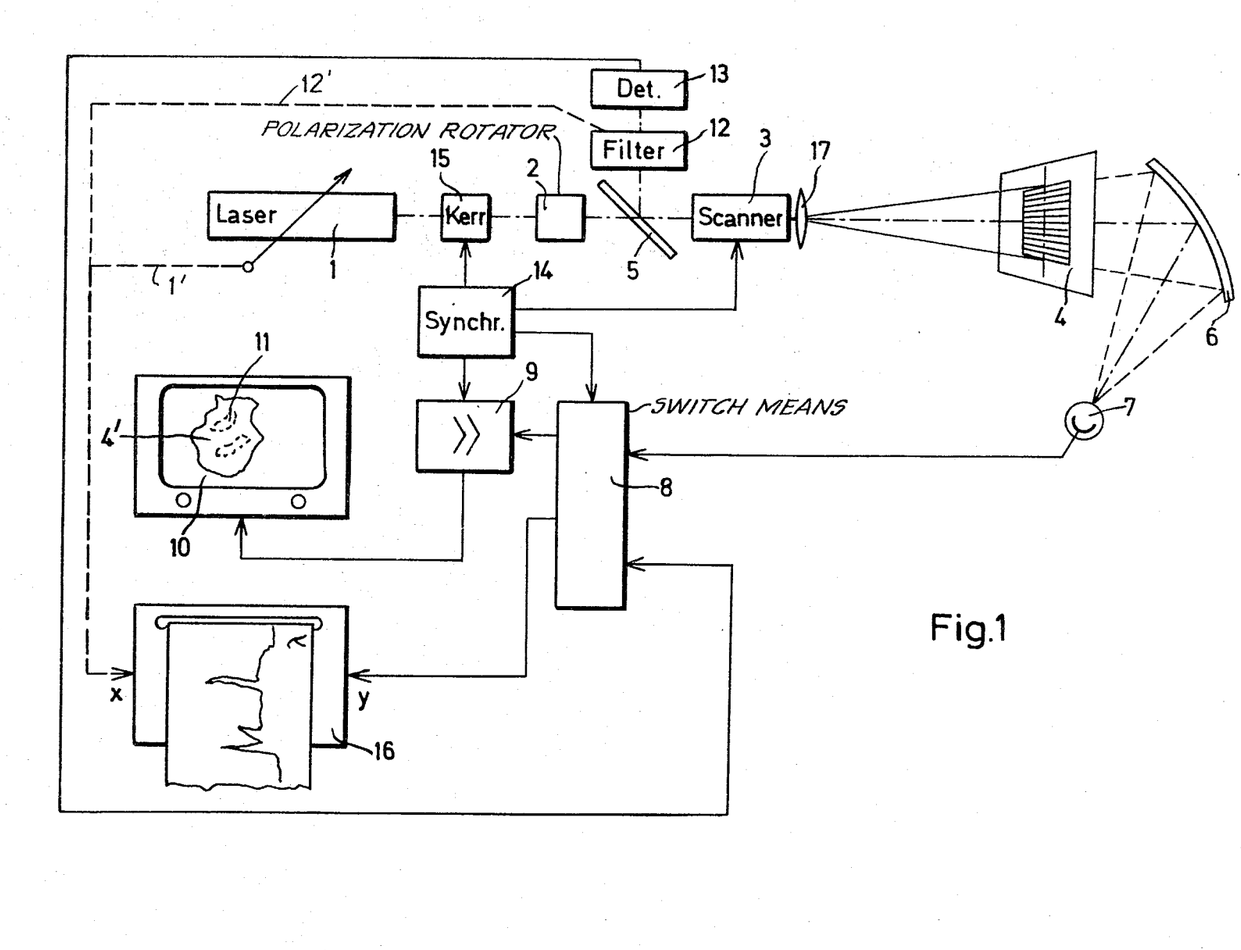
FIG. 1 schematically shows scanning-microscope apparatus for producing an image in inelastically scattered light, using a light source of preselectable wavelength.

In the scanning microscope of FIG. 1, a laser 1 produces a light bundle whose polarizing direction is adjustable at a polarization rotator 2; a slant arrow at laser 1 will be understood to symbolize a variable wavelength feature thereof. An objective lens 17 focuses the bundle in the plane of a transparent specimen 4, after passing through a splitting mirror 5, and after being subjected to raster displacement by a scanning unit 3, under synchronizing control by a synchronizing unit 14.

Transmitted radiation is reflected onto a detector 7 by a mirror 6 positioned behind the specimen 4. The output signal of the detector is fed via a switch element 8 to a video amplifier 9 which is synchronized with scanning frequency via unit 14, and the output signals of the video amplifier are used to display the specimen 4' on the screen of a monitor 10.

An electro-optical shutter, such as a Kerr cell 15, in the optical path between laser 1 and scanner 3 and under synchronizing control of unit 14, serves to blank the bundle of light for durations of scanner retrace.

Concurrently with detection of transmitted radiation at detector 7, Raman or fluorescence radiation emitted by the specimen is focused upon a much more sensitive detector 13, the path of focusing being via objective 17 and scanning unit 3, and being reflected out at splitting mirror 5 and filtered via a monochromator 12. Detector 13 may illustratively be a photomultiplier.

By suitable selection of the transmission characteristic of the filter 12 between specimen 4 and photomultiplier 13, with respect to the wavelength of laser 1, radiation (such as Raman or fluorescence radiation) which is characteristic of inclusions 11 in the specimen 4, passes to the photomultiplier 13 whose output signals serve, via switch element 8 and video amplifier 9, for the pictorial display of inclusions 11 at monitor 10.

The switch element 8 may include means for so chopping output signals of the photomultiplier 13 so that inclusions 11 are perceptible at monitor 10 by a blinking in the image 4' of the specimen 4.

The synchronizing unit 14 controls scanning unit 3, Kerr cell 15, and switch element 8 in synchronism with appropriate times or at desired times in the cycle of raster scanning. The unit 14 connection to scanning unit 3 may, for example, enable the scan to be stopped, with the laser light bundle remaining focused on a predetermined region (or regions) of the specimen, while Kerr cell 15 is unblanked and switch element 8 has connected the output of photomultiplier 13 to the input of a recorder 16.

The X-axis drive of recorder 16 may be so coupled with the control of instantaneous wavelength of laser (1) output as to enable a chart record (at 16) of the Raman spectrum of inclusions 11 in the specimen 4; in this event, in FIG. 1, a dashed-line connection 1' symbolizes the wavelength-synchronized feature.

Fluorescence and/or Raman spectra from individual regions of the specimen may, of course, also be obtained via a synchronizing connection 12' when a continuously variable monochromator 12 is used; in such case, wavelength selection is effected on the observation side of the apparatus, rather than on the excitation side.

Figure 2:
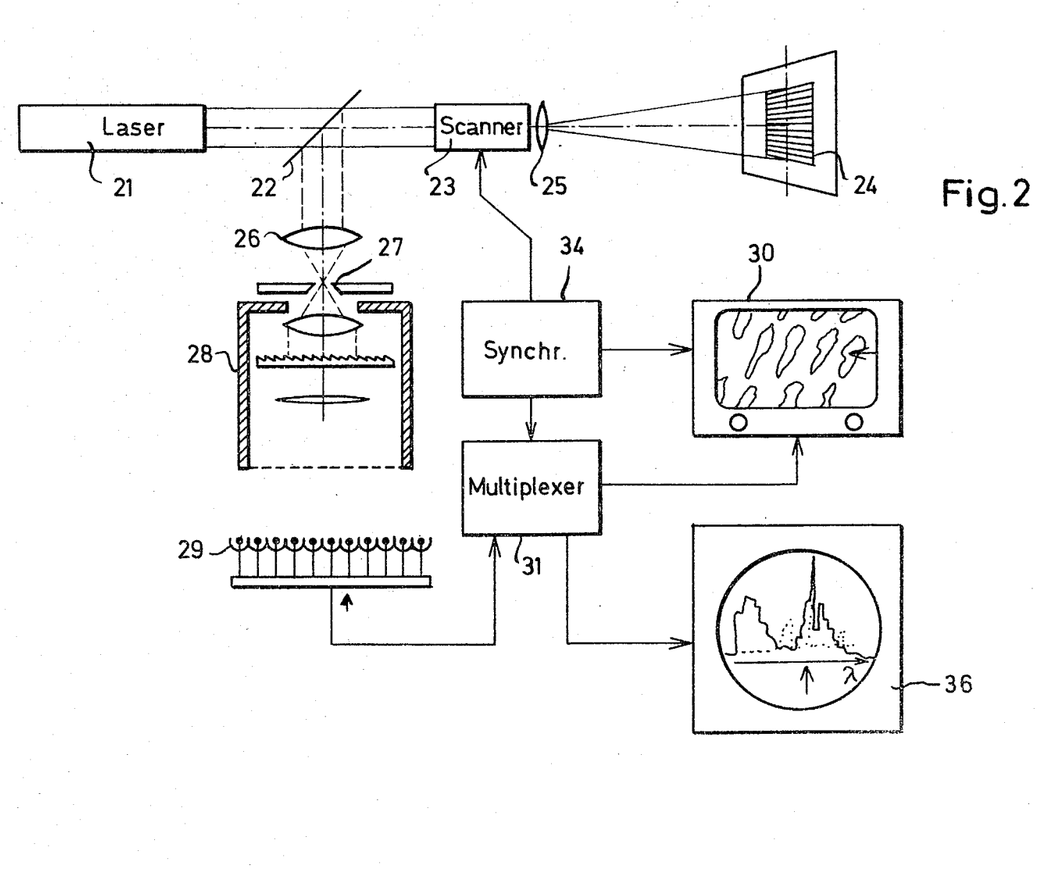
FIG. 2 similarly shows alternative apparatus with wavelength preselection on the observation side of the apparatus.

The apparatus schematically shown in FIG. 2 consists of a laser 21 with a semi-transmitting mirror 22 positioned in the laser-output path. A scanner 23 controlled by a synchronizing unit 34 moves the laser light beam (focused by an objective 25) over the specimen 24. Radiation emitted from a specimen 24 is collected by objective 25 and, after deflection at unit 24 and reflection by mirror 22, is focused by an optical system 26 on the entrance slit 27 of a monochromator 28 of the spectral-dispersion variety. Radiation components which are spectrally dispersed at 28 pass to an array of plural detectors 29, disposed behind a corresponding plurality of outlet openings of the monochromator 28, and the output signals of said detectors will be understood to serve for display of the spectrum of specimen 24 at a storage oscilloscope 36.

A control unit 31 contains a multiplexer, synchronized with the scanning frequency, for a reading of the detector array 29, as well as control electronics via which individual detector signals are selected and then are fed to a monitor 30, which is also synchronized with the scanning frequency. Monitor 30 shows images of the specimen 24 in the light of the particular characteristic spectral-response region of the selected detector.

In a storage oscilloscope 36 which is also synchronized with the scanning unit 23, the spectra of selected image points may be accumulated, by redundancy if desired, for each series of images, thereby improving their signal-to-noise ratio; alternatively, the total spectrum of specimen 24, integrated over all image points, may be displayed. Within the entire spectrum of the surface of the specimen, the band characteristic of the impurities can be so selected that only such fluorescent or Raman-active impurities 46 as are invisible upon ordinary observation can be recognized on the monitor 30.

Figure 3:
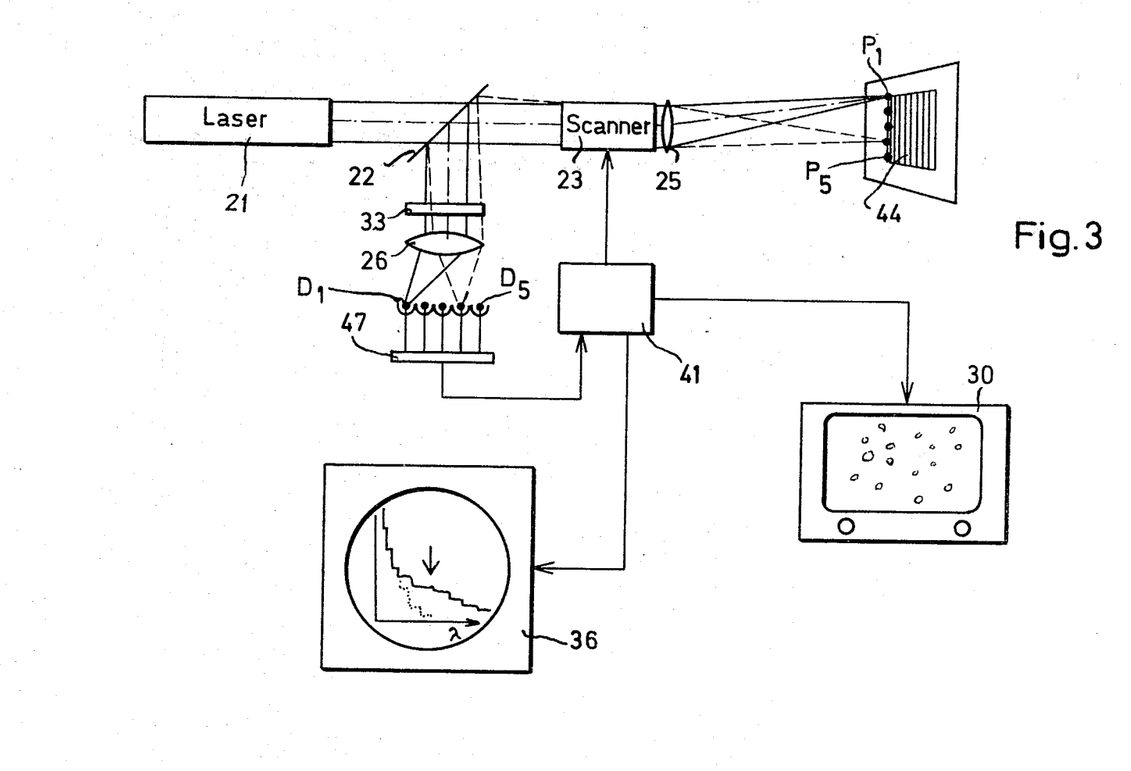
FIG. 3 similarly shows a third embodiment which permits the detection of dynamic processes.

With the arrangement shown in FIG. 3, fluorescent impurities can be detected even on a fluorescent specimen when only the fluorescence-fading time of the two components is different.

The construction of the FIG. 3 arrangement corresponds essentially to that shown in FIG. 2; however, in this case the illuminated points of a specimen 44 are focused on a linear detector-diode array rather than on the entrance slit 27 of the monochromator 28. A filter 33 arranged behind mirror 22 in the focusing optical path blocks out radiation of the source of light 21 and permits only fluorescence radiation of specimen 44 to fall on the detector-diode array 47.

The latter is so arranged that, for a given fixed position of a mirror in the deflecting scanner 23, the specimen point P1 which is just being illuminated is imaged on the first diode D1 of the array, and points P2 to P5 which are illuminated in time after this point P1 are focused on the corresponding adjacent diodes D2 to D5. The time variation of the intensity I(t) of fluorescence radiation of, for example, a specimen point $P_i$ can be determined from the signals $S_i$ of the diodes $D_i$ read out in phase with the scanning frequency, in accordance with the following equation:

$$I_{Pi}(t) = a \cdot S_{int}(i + V \cdot t/s)$$

In this equation, V is the scanning rate, s is the distance between two adjacent specimen points $P_i$ and a is a constant.

An electronic read-out and evaluation system 41 operating in synchronism with the scanning unit 23 prepares the signals of the diode array 47 as time-dependent signals of preselectable specimen points and conducts them to an oscilloscope 36 for display of the fading curve. The impurities which fluoresce with larger time constant than that of the specimen surface can be displayed separately on the monitor 30 in such manner that, by having the evaluator at 41 select certain diode groups of the array 47, there is an adjustment of the delay time between the illumination of a specimen point and the detection of fluorescence radiation therefrom. Fluorescence radiation can be distinguished from Raman radiation in the same manner.

Figure 4:
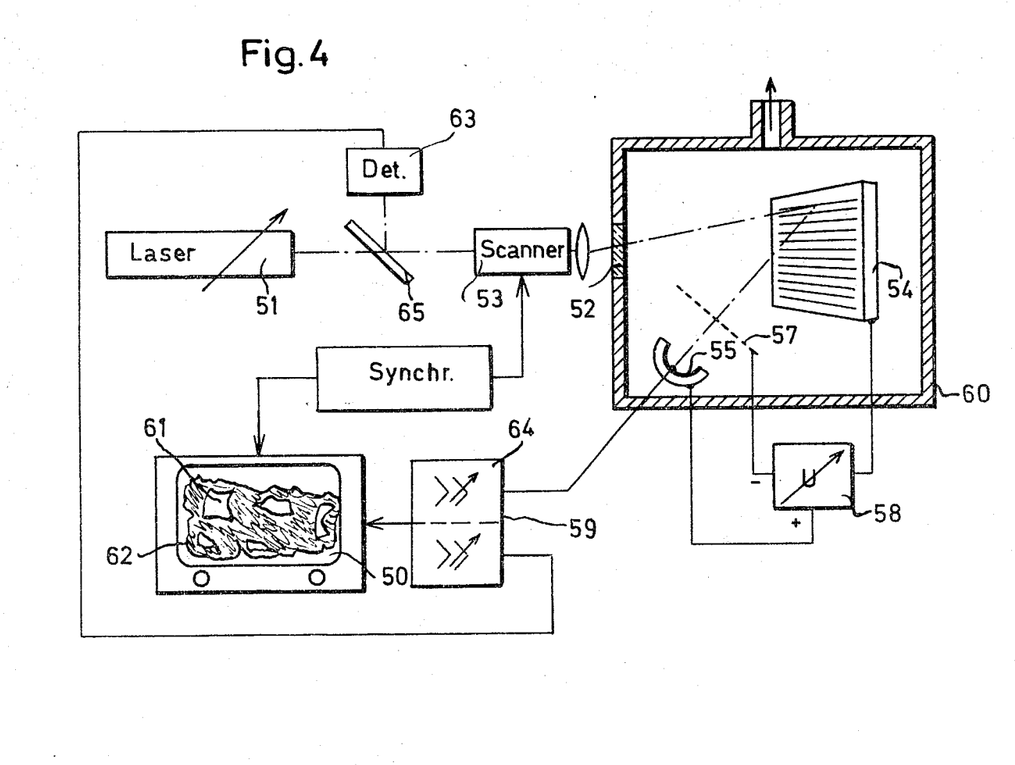
FIG. 4 similarly shows apparatus for producing an image of the two-dimensional distribution of emitted photo-electrons.

FIG. 4 schematically shows apparatus for displaying a specimen 54 in the "light" of its emitted photoelectrons. The specimen 54 is in an evacuated housing 60 in front of a window 52 through which it is irradiated with light from a laser 51. A scanner 53 deflects the laser light beam over the surface of the specimen. A detector 55 for photoelectrons emitted by the specimen is arranged within the housing 60. A power supply unit 58 maintains the detector at positive potential with respect to the specimen 54 and supplies a grid 57, located between detector 55 and specimen 54, with negative bias voltage relative to the specimen 54. After amplification in one channel of a two-channel amplifier 59, output signals of the detector 55 provide an image of electron-emitting specimen regions 61 on a monitor 50 which is synchronized with the scanner 53.

At monitor 50, regions 61 may be superposed on a bright-field vertical image 62 of the specimen 54, image 62 being produced by use of back-scattered light from the specimen 54 and reflected via a splitter mirror 65 to a detector 63, the output of detector 63 being connected with the second input of the two-channel amplifier 59.

By varying the excitation wavelength, the contrast of the image produced by the photoelectrons can be adjusted in a manner specific to the substance so that, for instance, a bright display appears only for all easily ionizable specimen-surface parts having electron-bond energy below a limit value which corresponds to the excitation wavelength.

A further contrasting aid then results from the grid 57 by which all electrons whose kinetic energy lies below a value defined by the bias voltage of grid 57 may be excluded from detection at 55. Having suitably selected the wavelength of the excitation light and the bias voltage of grid 57, electrons from a narrow energy window which is characteristic of the component of the specimen 54 to be made visible, are thereby selected for the production of the picture.

Figure 5:
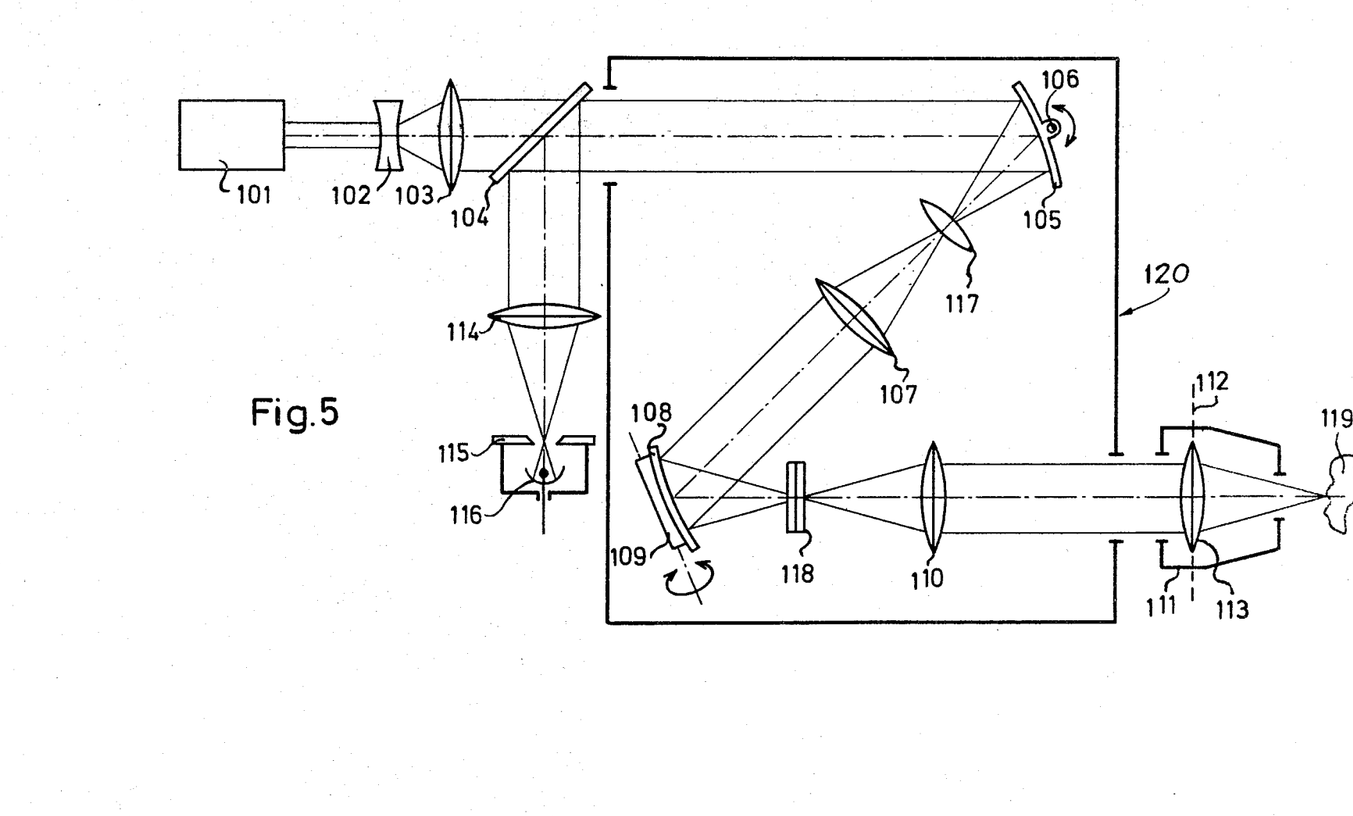
FIG. 5 schematically shows an optical system usable in the embodiments of FIGS. 1 to 4.

FIG. 5 shows in somewhat greater detail the construction of an optical system for any of the devices of FIGS. 1 to 4.

A laser light source 101 provides a monochromatic, parallel bundle of rays which is adapted by an optical expansion system 102, 103 to the diameter of an objective 111. After passing through a semi-transparent mirror 104, the expanded laser light beam enters a scanning unit 120 which has two pivoted concave mirrors 105 and 108, mounted with their pivot axes 106 and 109 perpendicular to each other, for orthogonal-line scanning of the object 119. Each of the concave mirrors 105 (108) focuses an incident parallel-ray illumination beam on the principal plane of a cylinder lens 117 (118) whose refractive power is so selected as a function of the time-/angle behavior of the mirrors that time-linear scanning takes place in the plane of the object 119.

Lenses 107 and 110, which have the same focal length as the mirrors 105 and 108, are positioned respectively between the two mirrors and between the mirror 108 and the objective 111, at a distance from the mirrors or from the picture-side principal plane 112 of the objective lens 113 which corresponds to twice their focal length. By means of the lenses 107 and 110, therefore, an imaging of the mirrors 105 and 109 occurs at one another and at the image-side principal plane 112 of objective 111, on a scale of −1. The objective 111 focuses the illumination ray bundle into the plane of the specimen surface 119.

The concave development of the mirrors is, of course, merely one possible development, although an advantageous one. Flat mirrors can also be used for the scanning, provided that additional refracting components are introduced into the optical path to provide the focusing action of the mirrors.

Due to the afocal beam path in the region of the scanning device 120, the construction of the latter is not limited by predetermined tube lengths but can be corrected within wide limits in combination with objectives which are corrected to infinite exit back-focus. Of course, it is also possible simply to select the refractive powers and spacings of the lenses in the scanning unit 120 in such manner that a beam path adapted to objectives with finite exit back-focus is obtained, instead of the afocal beam path shown here.

If suppression of wavelengths of the exciting light is necessary, suitable filters may be introduced into the optical path between mirror 104 and detector 116 (see filter 33 in FIG. 3) and/or a dichroitic splitting mirror may be used. Monochromator means can be disposed behind a diaphragm 115.

The above-described component arrangement in scanning device 120 assures that the axis of the scanning ray bundle always passes through the image-side principal point of the imaging objective 111, whose aperture is thus substantially completely filled at all scan-deflection angles. Scanning is thus effected in a refraction-limited manner, whereby a maximum amount of resolution is obtained. This being the case, the scanning device may be of comparably simple construction, permitting the integration of commercially available attachments (objectives, galvano-scanners) while avoiding complicated special manufacture.

Figure 6:
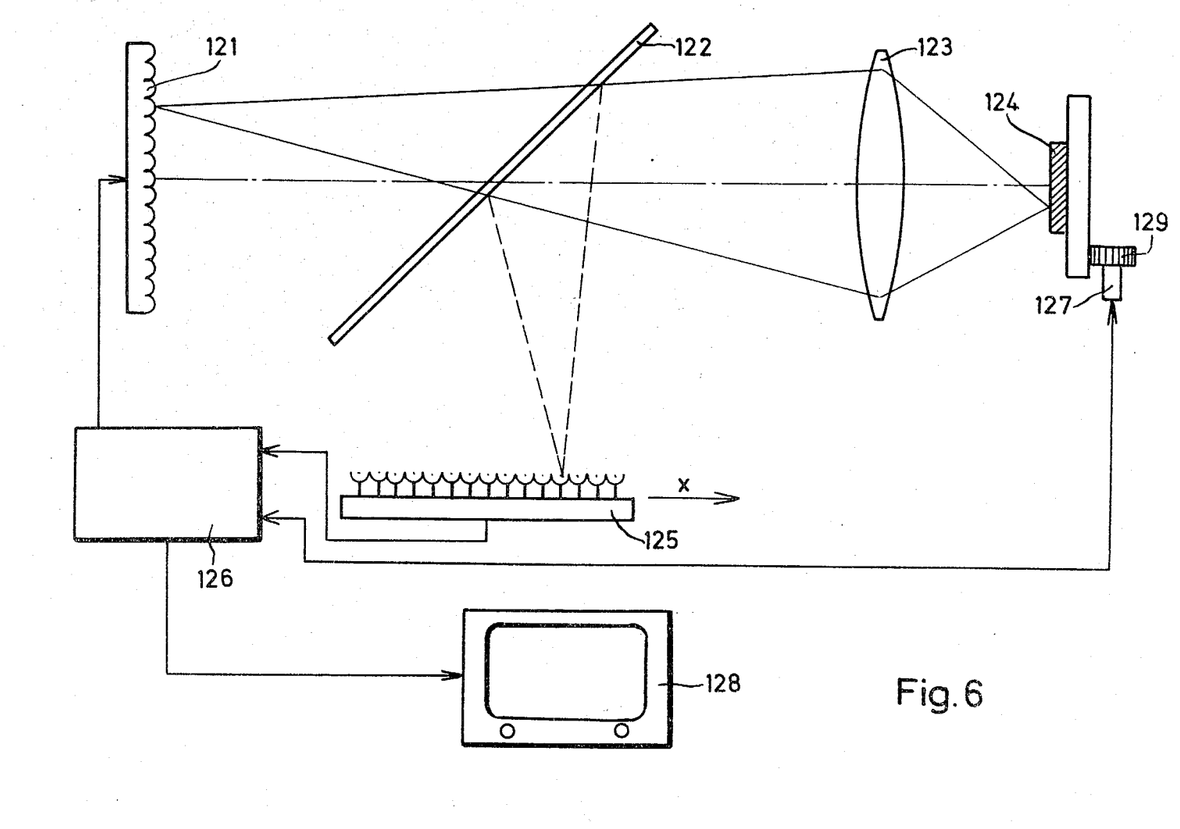
FIG. 6 schematically shows an alternative optical system which operates without a mechanical scanner.

In the embodiment of FIG. 6, a light-emitting diode array 121 is the source of light. The array 121 is focused by an objective 123 on the surface of a specimen 124 which under control of specimen-drive means 129, moves perpendicular to the plane of the paper. Upon sequential control by known electronic means 126 (not described in detail), the specimen is thus scanned line-by-line.

Radiation emitted from specimen 124 is so focused via objective 123 and splitting mirror 122 on a detector-diode array 125 that in each case a specimen point illuminated by the array 121 is imaged on a receiving diode at 125.

Since the control unit 126 scans or reads the "emitter array" 121 and the receiver array 125 synchronously, only radiation coming from the currently illuminated specimen point is detected; alternatively, it is possible, by introducing a phase delay between excitation and reading, to select radiation of delayed emission, as has already been described with reference to FIG. 3.

For a two-dimensional display of specimen 124 on the screen at monitor 128, the output signal of a position sensor 127 (coupled with the specimen drive 129) is suitably utilized in the control unit 126, in addition to output signals of the diode arrays 121 and 125.

In a modified FIG. 6 situation, the specimen drive can be dispensed with if the arrays 121 and 125 are developed two-dimensionally.

What is claimed is:

1. A method for the light-induced scanning-microscope display of specimen parameters and of their distribution, in which method the specimen is scanned in raster form on the illumination side by a beam of light, and radiation coming from the specimen is detected in phase with the raster, characterized by the fact that at least two different radiation components are detected, at least one of which radiation components lies in a spectral region not used on the illumination side and at least one of said components is focused, via the objective (17, 25, 113) used to focus the scanning beam and via the scanning unit (3, 23, 53, 120) used for its deflection, the focus being at a stationary receiver (13, 29, 47, 63, 116).

2. A method according to claim 1, characterized by the fact that that component of the radiation (a) emitted from the specimen (4, 24, 44) and (b) not contained in the spectral region used on the illumination side is focused at the receiver (13, 29, 47).

3. A method according to claim 1, characterized by the fact that at least two trains of signals are substantially simultaneously produced by detection of the scattered radiation, the transmitted radiation, the fluorescence radiation and/or the Raman radiation, and said at least two trains are used for production of the image.

4. A method according to claim 1, characterized by the fact that detection of the radiation not contained in the spectral region used on the illumination side is effected by a second receiver (55) which is independent of the illuminating optics.

5. A method according to claim 3, characterized by the fact that the images of the specimen (24, 44) which are produced in different spectral regions can be observed individually as desired.

6. A method according to claim 3, characterized by the fact that said signals produced in different spectral regions are displayed in superposed relation in one image (4', 11; 61, 62).

7. A method according to claim 6, characterized by the fact that said signals in different spectral regions used for the production of a superposed image (4', 11; 61, 62) are electronically controlled in their amplitude and/or phase.

8. A method according to claim 1, characterized by the fact that the illumination is effected by coherent light and that the light scattered by the specimen is superposed, prior to the detection, by light mirrored out from the illumination ray.

9. A method according to claim 1, characterized by the fact that the specimen to be examined is furthermore irradiated with ultrasonics.

10. A method according to claim 4, characterized by the fact that photoacoustic or photothermal signals coming from the substance are used for the image production.

11. A method according to claim 4, characterized by the fact that the specimen (54) to be tested is arranged in a vacuum and that electrons liberated from the surface of the substance by the light beam are used for image production.

12. A method according to claim 1, characterized by the fact that scanning movement of the light beam is stopped at predetermined points, and the spectral region used for the measurement or the spectral region of the illuminating light is varied.

13. A method according to claim 12, characterized by the fact that the image-point spacing of the raster is selected smaller than the diameter of the refraction-limited focus of the illumination beam, and that the substantially Gaussian intensity distribution of the light known there is used in order to develop an image-point-dependent distribution of signal intensity by means of an electronic computer in real time.

14. Apparatus for the light-induced scanning-microscope display of specimen parameters and of their distribution, in which apparatus the specimen is scanned on the illumination side by a beam of light, and radiation emitted by the specimen and not contained in the illumination-side spectral region is detected in phase with the scanning raster, characterized by the fact that, between the source of light and the specimen (4, 24, 44, 119) there are, first a splitting mirror (5, 22, 104), and then means (3, 23, 120) for the raster-like deflection of the beam of light, and then an objective (17, 25, 113) for focusing the light beam on the specimen, and further characterized by the fact that radiation coming from the specimen is focused on at least one stationary detector (13, 29, 47, 116), the latter focus being via the objective (17, 25, 113), the deflection means (3, 23, 120), and the splitter mirror (5, 22,104).

15. Apparatus according to claim 14, characterized by the fact that between the splitter mirror (104) and the detector (116) a stationary diaphragm (115) as well as a continuously variable monochromator are arranged.

16. Apparatus according to claim 14, characterized by the fact that between the splitting mirror (22) and the detector there are arranged a stationary diaphragm (27) as well as a monochromator (28) for simultaneous imaging of the light coming from different spectral regions onto a plurality of receivers (29) associated with the corresponding spectral regions.

17. Apparatus for the light-induced scanning-microscope display of specimen parameters and of their distribution, in which apparatus the sample is scanned on the illumination side by a beam of light, and sample-emitted radiation which is not contained in the illumination-side spectral region is detected in phase with the scanning raster, characterized by the fact that, between the source of light and the specimen (4, 24, 44, 119), there are, first, a splitting mirror (5, 65, 104), and then means (3, 23, 120) for the raster-like deflection of the beam of light, and then an objective (113) of focusing the light beam on the specimen, further characterized by the fact that radiation coming from the specimen is focused via the objective, the deflection means and the splitting mirror on at least one first stationary detector (63), and further characterized by the fact that at least one second receiver (55) sensitized to radiation outside the spectral region used for illumination is positioned outside of the optical system containing the deflection unit (53) in front of or behind the specimen (54).

18. Apparatus according to claim 14, characterized by a diaphragm disposed in front of the detector and displaceable perpendicular to the optical axis.

19. Apparatus according to claim 14, characterized by a diaphragm of variable dimension arranged in front of the detector.

20. Apparatus according to claim 14, characterized by the fact that a linear diode array (47) extending in the scanning direction is used as a receiver.

21. Apparatus according to claim 14, characterized by the fact that a laser (1, 21, 35, 51, 101) is used as the light source.

22. Apparatus according to claim 21, characterized by a continuously variable laser (1, 51) for the production of light of a plurality of several preselectable wavelengths.

23. Apparatus according to claim 21, characterized by the fact that a pulsed laser is used as the light source.

24. Apparatus according to any of claim 14, characterized by the fact that light-emitting diodes are used as the source of light.

25. Apparatus for the carrying out of the method of claim 1, characterized by the fact that the substance to be examined is arranged in the specimen chamber of a known scanning electron microscope.

26. Apparatus according to claim 14, characterized by the fact that the scanning unit (120) has ray-deflecting surfaces (105, 108) arranged in the immediate vicinity of planes conjugate to the image-side principal plane (112) of the objective (113) used for the imaging, and that beam deflection in the scanning unit (120) is afocal.

27. Apparatus for the light-induced scanning-microscope display of parameters and of their distribution, in which apparatus the specimen is scanned on the illumination side by a beam of light, and radiation emitted from the specimen and not contained in the illumination-side spectral region is detected in phase with the scanning raster, characterized by the fact that behind a light-emitting diode array (121) as the source of light, there are arranged a splitting mirror (122) and, following it, an objective (123) for focusing the source of light (121) into the object plane, further characterized by the fact that radiation coming from the specimen (124) is focused by the objective (123) and the splitting mirror (122) onto a detector diode array (125), and that an electronic arrangement (126) is provided for synchronous scanning of diodes (127, 128) on the two arrays (121, 125) conjugated in each case by the optics (122, 123).

* * * * *